(12) United States Patent
Storey et al.

(10) Patent No.: US 9,150,672 B2
(45) Date of Patent: Oct. 6, 2015

(54) IN SITU FORMATION OF HYDROXY CHAIN END FUNCTIONAL POLYOLEFINS

(71) Applicant: The University of Southern Mississippi, Hattiesburg, MS (US)

(72) Inventors: Robson F. Storey, Hattiesburg, MS (US); David L. Morgan, Fairfield, CA (US)

(73) Assignee: The University of Southern Mississippi, Hattiesburg, MS (US)

( * ) Notice: Subject to any disclaimer, the term of this patent is extended or adjusted under 35 U.S.C. 154(b) by 295 days.

(21) Appl. No.: 13/767,630

(22) Filed: Feb. 14, 2013

(65) Prior Publication Data

US 2013/0158206 A1 Jun. 20, 2013

Related U.S. Application Data

(62) Division of application No. 12/534,081, filed on Jul. 31, 2009, now Pat. No. 8,394,898.

(51) Int. Cl.
| | | |
|---|---|---|
| *C08F 10/10* | (2006.01) | |
| *C07D 207/325* | (2006.01) | |
| *C07D 207/335* | (2006.01) | |
| *C08F 110/10* | (2006.01) | |

(52) U.S. Cl.
CPC ............ *C08F 10/10* (2013.01); *C07D 207/325* (2013.01); *C07D 207/335* (2013.01); *C08F 110/10* (2013.01)

(58) Field of Classification Search
CPC ... C08F 110/10; C08F 10/10; C07D 207/325; C07D 207/335
USPC ............................................. 525/375, 333.7
See application file for complete search history.

(56) References Cited

U.S. PATENT DOCUMENTS

| | | |
|---|---|---|
| 3,632,600 A | 1/1972 | Morris et al. |
| 3,756,793 A | 9/1973 | Robinson et al. |
| 4,191,537 A | 3/1980 | Lewis et al. |
| 4,342,849 A | 8/1982 | Kennedy |
| 4,486,572 A | 12/1984 | Kennedy |
| 4,758,631 A | 7/1988 | Kennedy et al. |
| 4,814,405 A | 3/1989 | Kennedy |
| 4,910,321 A | 3/1990 | Kennedy et al. |
| 4,943,616 A | 7/1990 | Mishra et al. |
| 4,946,899 A | 8/1990 | Kennedy et al. |
| 5,004,478 A | 4/1991 | Vogel et al. |
| 5,032,653 A | 7/1991 | Cheradame et al. |
| 5,122,572 A | 6/1992 | Kennedy et al. |
| 5,169,914 A | 12/1992 | Kaszas et al. |
| 5,225,492 A | 7/1993 | Kennedy et al. |
| 5,340,881 A | 8/1994 | Kennedy et al. |
| 5,350,819 A | 9/1994 | Shaffer |
| 5,395,885 A | 3/1995 | Kennedy et al. |
| 5,444,135 A | 8/1995 | Cheradame et al. |
| 5,448,000 A | 9/1995 | Gullapalli et al. |
| 5,451,647 A | 9/1995 | Faust et al. |
| 5,506,316 A | 4/1996 | Shaffer |
| 5,580,935 A | 12/1996 | Shaffer |
| 5,629,394 A | 5/1997 | Cheradame et al. |
| 5,663,470 A | 9/1997 | Chen et al. |
| 5,690,861 A | 11/1997 | Faust |
| 5,777,044 A | 7/1998 | Faust |
| 5,945,491 A | 8/1999 | Matyjaszewski et al. |
| 6,033,446 A | 3/2000 | Cherpeck et al. |
| 6,194,597 B1 | 2/2001 | Faust et al. |
| 6,407,066 B1 | 6/2002 | Dressen et al. |
| 6,515,083 B2 | 2/2003 | Ozawa et al. |
| 6,602,965 B1 | 8/2003 | Terazawa et al. |
| 6,642,318 B1 | 11/2003 | Chiefari et al. |
| 6,753,391 B1 | 6/2004 | Lewandowski et al. |
| 6,818,716 B2 | 11/2004 | Wendland et al. |
| 6,969,744 B2 | 11/2005 | Stokes et al. |
| 7,576,161 B2 | 8/2009 | Stokes |
| 2004/0260033 A1* | 12/2004 | Stokes et al. ................... 525/375 |
| 2006/0041081 A1 | 2/2006 | Stokes et al. |
| 2006/0264577 A1 | 11/2006 | Faust et al. |
| 2010/0249001 A1* | 9/2010 | Storey et al. ................... 508/268 |

FOREIGN PATENT DOCUMENTS

| | | |
|---|---|---|
| EP | 0206756 | 6/1986 |
| EP | 0341012 | 11/1989 |
| EP | 0356726 | 3/1990 |
| EP | 0382159 | 8/1990 |
| EP | 0397081 | 11/1990 |
| SU | 293804 | 1/1970 |
| WO | WO 99/09074 | 2/1999 |

OTHER PUBLICATIONS

Cirpan et al., "Synthesis and electroactivity of pyrrole end-functionalized poly(2-methyl-2-oxazoline)," European Polymer Journal 37, 2225-2229, 2001.

Faust et al., "Living carbocationic polymerization. XXI. Kinetic and mechanistic studies of isobutylene polymerization initiated by trimethylpentyl esters of different acids," J. Macromol. Sci.-Chem. A27(6), 649-667, 1990.

Fodor et al., "Synthetic applications of non-polymerizable monomers in living carbocationic polymerizations," Polymer Reprints 35, 492-493, 1994.

(Continued)

*Primary Examiner* — Ling Choi
*Assistant Examiner* — Chun-Cheng Wang
(74) *Attorney, Agent, or Firm* — Jones Day

(57) ABSTRACT

Provided herein are methods for preparing a telechelic polymer of formula I

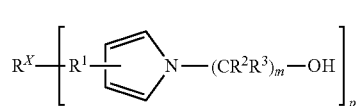

wherein:
  $R^1$ is a polyolefin group;
  $R^2$ and $R^3$ are, independently in each —$(CR^2R^3)$— unit, hydrogen or alkyl from 1 to 6 carbons;
  m is an integer from 2 to 20;
  $R^X$ is a cationic initiator residue; and
  p is an integer from 1 to 4.

20 Claims, No Drawings

(56) References Cited

OTHER PUBLICATIONS

Hadjikyriacou et al., "Cationic macromolecular design and synthesis using furan derivatives," Macromolecules 32, 6393-6399, 1999.

Hadjikyriacou et al., "Living coupling reaction in living cationic polymerization. 3. Coupling reaction of living polyisobutylene using bis(furanyl) derivatives," Macromolecules 33, 730-733, 2000.

Hadjikyriacou et al., "Living coupling reaction in living cationic polymerization. 4. Synthesis of telechelic polyisobutylenes using bis-furanyl derivatives as coupling agents," Pure Appl. Chem. A37, 1333-1352, 2000.

Ivan et al., "Living carbocationic polymerization. XXX. One-pot synthesis of allyl-terminated linear and tri-arm star polyisobutylenes, and epoxy- and hydroxy-telechelics therefrom," J. Polymer Sci. Part A. Polymer Chem. 28, 89-104, 1990.

Keaton, "Living Ziegler-Natta polymerization," http://www.organicdivision.org/ama/orig/Fellowship/2002_2003_Awardees/Essays/keaton.pdf.

Kennedy et al., "Living carbocationic polymerization. XXXIX. Isobutylene polymerization in the presence of pyridine and various other electron donors," J. Macromol. Sci.-Chem. A28, 197-207, 1991.

Koroskenyi et al., "Initiation via haloboration in living cationic polymerization. 6. A novel method for the synthesis of primary amine functional polyisobutylenes," Pure Appl. Chem. A36(12), 1879-1893, 1999.

Machl et al., "Novel synthetic routes to aminfunctionalized polyisobutylenes," Polymer Reprints 44(2), 858-859, 2003.

Martinez-Castro et al., "Primary halide-terminated polyisobutylene: End-quenching of quasiliving carbocationic polymerization with $N$-(w-haloalkyl)pyrrole," Macromolecules 42, 4963-4971. 2009.

Morgan et al., "Primary hydroxy-terminated polyisobutylene via end-quenching with a protected $N$-(w-hydroxyalkyl)pyrrole," Macromolecules 43, 1329-1340, 2010.

Percec et al., "New telechelic polymers and sequential copolymers by polyfunctional initiator-transfer agents (Inifers) 29. Synthesis of $\alpha,\omega$-di(amino)polyisobutylenes," Polymer Bulletin 9, 27-32, 1983.

Roth et al., "A novel method of the determination of propagation rate constants: Carbocationic oligomerization of isobutylene," Macromolecules 29(19), 6104-6109, 1996.

Sawamoto et al., "End-functionalized polymers by living cationic polymerization. 1. Mono- and bifunctional poly(vinyl ethers) with terminal malonate or carboxyl groups," Macromolecules 20, 1-6, 1987.

Simison et al., "End-quenching of quasiliving carbocationic isobutylene polymerization with hindered bases: Quantitative formation of exo-olefin-terminated polyisobutylene," Macromolecules, 39 2481-2487, 2006.

Storey et al., "$N$-Methylpyrrole-terminated polyisobutylene through end-quenching of quasiliving carbocationic polymerization," Macromolecules 38, 4618-4624, 2005.

Notice of Allowability mailed May 11, 2005, U.S. Appl. No. 10/600,898.

Office Action mailed Apr. 1, 2008, U.S. Appl. No. 11/186,157.

Office Action mailed Oct. 20, 2008, U.S. Appl. No. 11/186,157.

Office Action mailed Feb. 20, 2009, U.S. Appl. No. 11/186,157.

Office Action mailed Jun. 25, 2012, U.S. Appl. No. 12/415,829.

\* cited by examiner

IN SITU FORMATION OF HYDROXY CHAIN END FUNCTIONAL POLYOLEFINS

CROSS REFERENCE TO RELATED APPLICATION

This application is a divisional application of U.S. patent application Ser. No. 12/534,081, filed Jul. 31, 2009, the disclosure of which is incorporated herein by reference int its entirety.

FIELD

Provided herein are methods for the preparation of hydroxy-terminated polyolefins via in situ functionalization of quasiliving polyolefins.

BACKGROUND

Hydroxy-terminated polymers, that is, polymers containing hydroxy end groups, are useful intermediates in the preparation of high-performance polymer products. Such intermediates can be useful, for example, in the production of fuel or lube oil additives, thermoplastic elastomers such as polyurethanes, poly(urethane-urea)s, or polyamides, network polymers, star branched polymers, and block copolymers. Thus, there is a need for hydroxyl-terminated polymers, as well as convenient methods of producing the same.

Prior methods for synthesizing hydroxy-terminated polyisobutylene have involved post-polymerization modification of telechelic polyisobutylene, for example, by hydroboration oxidation of olefin-terminated polyisobutylene. Described herein are methods for the in situ functionalization of quasiliving polyolefins, including polyisobutylene.

SUMMARY

Provided herein are methods for preparing a telechelic polymer of formula I:

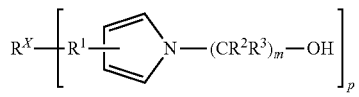

or a mixture thereof,
wherein $R^1$ is a polyolefin group,
$R^2$ and $R^3$ are, independently in each —$(CR^2R^3)$— unit, hydrogen or alkyl from 1 to 6 carbons;
m is an integer from 2 to 20;
$R^X$ is a cationic initiator residue; and
p is an integer from 1 to 4;
comprising:
(a) generating a quasiliving carbocationic polyolefin in a quasiliving reaction system;
(b) adding to the quasiliving reaction system of step (a) a compound of formula II:

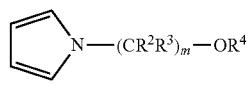

wherein $R^4$ is alkyl, alkenyl, alkynyl, aryl, alkaryl, aralkyl, —$C(O)R^5$; —$SO_3R^6$, —$SO_2R^7$, or —$Si(R^8)(R^9)(R^{10})$ wherein $R^5$, $R^6$, $R^7$, $R^8$, $R^9$, and $R^{10}$ are each, independently, alkyl or aryl
to form one or more intermediate(s);
and
(c) contacting the one or more intermediate(s) from step (b) with one or more acid(s) in situ to form the telechelic polymer of formula I.

Further, provided herein are compounds of formula I:

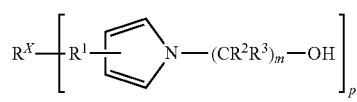

wherein:
$R^1$ is a polyolefin group;
$R^2$ and $R^3$ are, independently in each —$(CR^2R^3)$— unit, hydrogen or alkyl from 1 to 6 carbons;
m is an integer from 2 to 20;
$R^X$ is a cationic initiator residue; and
p is an integer from 1 to 4.

DETAILED DESCRIPTION

(a) Definitions

Unless defined otherwise, all technical and scientific terms used herein have the same meaning as commonly understood by one of ordinary skill in the art. In the event that there are a plurality of definitions for a term used herein, the definitions provided in this section prevail unless stated otherwise.

As used herein, "polyolefin group" refers to a monovalent or divalent polyolefin substituent. In some embodiments, the polyolefin group is a polyisobutyl group or a polyisobutylene group.

As used herein, "polyolefin" refers to a polymer that comprises at least two olefin monomer units. In some embodiments, the polyolefin has a molecular weight from about 300 to in excess of a million g/mol. In some embodiments, the polyolefin has a molecular weight of from about 200 to 10,000 g/mol. In some embodiments, the polyolefin has a molecular weight of from about 1,000 to 5,000 g/mol. In some embodiments, the polyolefin has a molecular weight of from about 2,000 to 3,000 g/mol. In some embodiments, the polyolefin has a molecular weight of from about 100,000 to 1,000,000 g/mol. In some embodiments, the polyolefin has a molecular weight greater than 200 g/mol. In some embodiments, the polyolefin has a molecular weight greater than 400 g/mol. In some embodiments, the polyolefin has a molecular weight greater than 600 g/mol. In some embodiments, the polyolefin has a molecular weight greater than 800 g/mol. In some embodiments, the polyolefin has a molecular weight greater than 1,000 g/mol. In some embodiments, the polyolefin has a molecular weight greater than 5,000 g/mol. In some embodiments, the polyolefin has a molecular weight greater than 10,000 g/mol. In some embodiments, the polyolefin has a molecular weight greater than 100,000 g/mol. In some embodiments, the polyolefin has a molecular weight greater than 500,000 g/mol. In some embodiments, the polyolefin has a molecular weight greater than 1,000,000 g/mol. In some embodiments, the polyolefin is derived from a mono-functional initiator, bi-functional initiator, or multi-functional initiator. In some embodiments, the polyolefin is polyisobutene.

As used herein, "polyisobutyl group" refers to a monovalent polyolefin group comprising at least 2 isobutylene monomer units. In some embodiments, the polyisobutyl group is

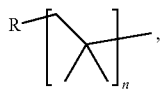

wherein R is H or alkyl of 1 to about 10 carbons, and n is an integer from about 10 to about 2000. In further embodiments, n is about 10 to about 1000. In further embodiments, n is about 10 to about 500. In further embodiments, n is about 10 to about 250. In further embodiments, n is about 10 to about 100. In further embodiments, n is about 10 to about 50.

As used herein, "polyisobutylene group" refers to a divalent polyolefin group comprising at least 2 isobutylene monomer units. In some embodiments, the polyisobutylene group is

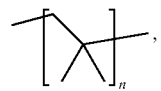

wherein n is an integer from about 10 to about 2000. In further embodiments, n is about 10 to about 1000. In further embodiments, n is about 10 to about 500. In further embodiments, n is about 10 to about 250. In further embodiments, n is about 10 to about 100. In further embodiments, n is about 10 to about 50.

As used herein, "cationic initiator residue" refers to a mono or polyvalent radical of formula $(-CR_aR_b)_rR_c$, wherein $R_a$ and $R_b$ are each independently hydrogen, alkyl, aryl, alkaryl, or aralkyl, provided that at least one of $R_a$ and $R_b$ is not hydrogen, and $R_c$ is an aliphatic or aromatic univalent or polyvalent radical with valence r, wherein r is an integer from 1 to 4. In some embodiments, $R_c$ is hydrocarbyl. In some embodiments, $R_c$ is aryl. In some embodiments, $R_c$ is alkyl. In some embodiments, $R_c$ is phenyl. In some embodiments, r is 1. In some embodiments, r is 2. In some embodiments, r is 3. In some embodiments, r is 4. In some embodiments, the carbocationic initiator residue is derived from an initiator described herein.

As used herein, "alkyl" refers to a uni-valent hydrocarbon group of about 1 to about 20 carbons. In some embodiments, the alkyl group contains about 1 to about 15 carbons. In some embodiments, the alkyl group contains about 1 to about 10 carbons. In some embodiments, the alkyl group contains about 1 to about 8 carbons. In some embodiments, the alkyl group contains about 1 to about 6 carbons. In some embodiments, the alkyl group contains about 1 to about 3 carbons. In some embodiments, the alkyl group contains 1 to 2 carbons. In some embodiments, the alkyl group is primary. In some embodiments, the alkyl group is secondary. In some embodiments, the alkyl group is tertiary. In some embodiments, the alkyl group is methyl, ethyl, n-propyl, isopropyl, isobutyl, n-butyl, sec-butyl, tert-butyl, isopentyl, neopentyl, tert-pentyl, or isohexyl. In some embodiments, the alkyl group is methyl, ethyl, n-propyl, or isopropyl. In some embodiments, the alkyl group is methyl. In some embodiments, the alkyl group is tert-butyl. In some embodiments, the alkyl group is a straight hydrocarbon chain. In some embodiments, the alkyl group is a branched hydrocarbon chain. In some embodiments, the alkyl group is cyclic. In some embodiments, the alkyl group is substituted.

As used herein, "alkenyl" refers to a uni-valent hydrocarbon group of 2 to about 20 carbons, wherein the chain or group contains one or more double bonds. In some embodiments, the alkenyl group contains 2 to about 15 carbons. In some embodiments, the alkenyl group contains 2 to about 10 carbons. In some embodiments, the alkenyl group contains 2 to about 8 carbons. In some embodiments, the alkenyl group contains 2 to about 6 carbons. In some embodiments, the alkenyl group contains 2 to 3 carbons. In some embodiments, the alkenyl group is an allyl group. In some embodiments, the alkenyl group contains one or more double bonds that are conjugated to another unsaturated group. In some embodiments, the alkenyl group is substituted.

As used herein, "alkynyl" refers to a uni-valent hydrocarbon group of 2 to about 20 carbons, wherein the chain contains one or more triple bonds. In some embodiments, the alkynyl group contains 2 to about 15 carbons. In some embodiments, the alkynyl group contains 2 to about 10 carbons. In some embodiments, the alkynyl group contains 2 to about 8 carbons. In some embodiments, the alkynyl group contains 2 to about 6 carbons. In some embodiments, the alkynyl group contains 2 to 3 carbons. In some embodiments, the alkynyl group is a propargyl group. In some embodiments, the alkynyl group contains one or more triple bonds that are conjugated to another unsaturated group. In some embodiments, the alkynyl group is substituted.

As used herein, "aryl" refers to a uni-valent monocyclic or multicyclic aromatic group containing from 6 to about 30 carbons. In some embodiments, the aryl group is monocyclic. In some embodiments, the aryl group contains 6 to about 15 carbons. In some embodiments, the aryl group contains 6 to about 10 carbons. In some embodiments, the aryl group is fluorenyl, phenyl, or naphthyl. In some embodiments, the aryl group is phenyl. In some embodiments, the aryl is substituted.

As used herein, "alkaryl" refers to a uni-valent aryl group substituted with at least one alkyl, alkenyl, or alkynyl group.

As used herein, "aralkyl" refers to a uni-valent alkyl, alkenyl, or alkynyl group substituted with at least one aryl group.

As used herein, "substituted" refers to the presence of one or more substituents. In some embodiments, only one substituent is present.

As used herein, "quasiliving carbocationic polyolefin" refers to a carbocationic polyolefin formed under polymerization conditions such that a polymerization proceeds with minimal irreversible chain termination and minimal chain transfer. Such polymerizations are known as "quasiliving polymerizations," and proceed by initiation followed by propagation, wherein propagating (active) species are in equilibrium with non-propagating (dormant) polymer chains.

As used herein, "quasiliving reaction system" refers to any reaction system suitable to carry out a quasiliving polymerization. In some embodiments, the reaction system comprises one or more Lewis acids, a monomer, initiator, and electron donor. In some embodiments, the reaction system comprises a common ion salt or common ion salt precursor. In some embodiments, the reaction system comprises a diluent.

As used herein, "Lewis acid" refers to a chemical entity that is capable of accepting a pair of electrons.

As used herein, "monomer" refers to an olefin that is capable of combining with a carbocation to form another carbocation.

As used herein, "initiator" refers to a compound that provides a carbocation.

As used herein, "electron donor" refers to a molecule that is capable of donating a pair of electrons to another molecule.

As used herein, "common ion salt" refers to an ionic salt that is optionally added to a reaction performed under quasiliving carbocationic polymerization conditions to prevent dissociation of the propagating carbenium ion and counterion pairs.

As used herein, "common ion salt precursor" refers to an ionic salt that is optionally added to a reaction performed under quasiliving carbocationic polymerization conditions, wherein the ionic salt generates counter-anions that are identical to those of the propagating chain ends, via in situ reaction with a Lewis acid.

As used herein, "halide" refers to halogen. In some embodiments, halogen is F, Cl, Br, or I. In some embodiments, halogen is F. In some embodiments, halogen is Cl. In some embodiments, halogen is Br. In some embodiments, halogen is I.

As used herein, "contacting" refers to bringing two or more compounds into physical contact with each other. In some embodiments, two or more compounds react with each other when contacted.

As used herein, "reacting" refers to contacting two or more compounds with each other, wherein at least one of said two or more compounds is chemically transformed into a different compound.

As used herein, "alkyl aluminum halide" refers to a compound of formula $R_nAlX_{3-n}$, wherein n is 1, 1.5, or 2; R is an alkyl group; and X is a halogen, and mixtures thereof.

As used herein, "about" refers to up to plus or minus 10% of the indicated number. For example, "about 25° C." refers to 22.5° C. to 27.5° C. In some embodiments, about refers to up to plus or minus 9, 8, 7, 6, 5, 4, 3, 2, or 1% of the indicated number. When only integer values are possible, "about" refers to up to plus or minus 10% rounded to the nearest integer number. For example, "about 9 carbons" refers to 8-11 carbons.

As used herein, "in situ" refers to a step performed in the same reaction system. For the methods described herein, contacting the one or more intermediate(s) from step (b) with one or more acid(s) in situ means that the one or more acid(s) is/are contacted with the one or more intermediate(s) in the same reaction system where steps (a) and (b) were performed, and prior to termination.

(b) Methods

Provided herein are methods for preparing a telechelic polymer of formula I:

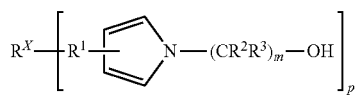

or a mixture thereof,
wherein $R^1$ is a monovalent polyolefin group,
$R^2$ and $R^3$ are, independently in each —$(CR^2R^3)$— unit, hydrogen or alkyl from 1 to 6 carbons;
m is an integer from 2 to 20;
$R^X$ is a cationic initiator residue; and
p is an integer from 1 to 4;
comprising:
(a) generating a quasiliving carbocationic polyolefin in a quasiliving reaction system;
(b) adding to the quasiliving reaction system of step (a) a compound of formula II:

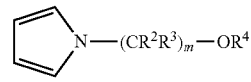

wherein $R^4$ is alkyl, alkenyl, alkynyl, aryl, alkaryl, aralkyl, —C(O)$R^5$; —SO$_3R^6$, —SO$_2R^7$, or —Si($R^8$)($R^9$)($R^{10}$) wherein $R^5$, $R^6$, $R^7$, $R^8$, $R^9$, and $R^{10}$ are each, independently, alkyl or aryl to form one or more intermediate(s);
and
(c) contacting the one or more intermediate(s) from step (b) with one or more acid(s) in situ to form the telechelic polymer of formula I.

Without being bound or limited to any theory, in some embodiments, the compound of formula II reacts with the quasiliving carbocationic polyolefin to form the one or more intermediate(s). Without being bound or limited to any theory, in some embodiments, the one or more intermediate(s) is or includes a compound of formula III.

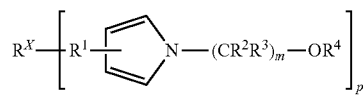

In some embodiments, greater than or equal to 80% of the compound of formula III is consumed by the one or more acid(s) of step (c). In some embodiments, greater than or equal to 85% of the compound of formula III is consumed by the one or more acid(s) of step (c). In some embodiments, greater than or equal to 90% of the compound of formula III is consumed by the one or more acid(s) of step (c). In some embodiments, greater than or equal to 95% of the compound of formula III is consumed by the one or more acid(s) of step (c). In some embodiments, greater than or equal to 98% of the compound of formula III is consumed by the one or more acid(s) of step (c).

Without being bound or limited to any theory, in some embodiments, the one or more intermediate(s) is or includes a compound of formula IV.

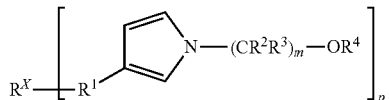

Without being bound or limited to any theory, in some embodiments, the one or more intermediate(s) is or includes a compound of formula V

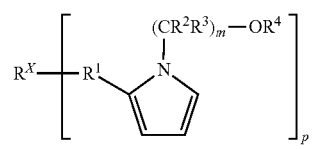

Without being bound to or limited to any theory, in some embodiments, the one or more intermediate(s) is or includes a compound of formula VI.

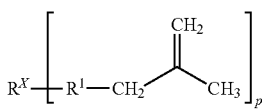

VI

Without being bound or limited to any theory, in some embodiments, the quasiliving carbocationic polyolefin reacts with the compound of formula II to form a mixture comprising a compound of formula IV, V, and VI.

Without being bound or limited to any theory, in some embodiments, the one or more intermediate(s) reacts with the one or more acid(s) of step (c) to form the telechelic polymer of formula I.

Without being bound or limited to any theory, in some embodiments, the one or more acid(s) of step (c) reacts with the compound of formula IV

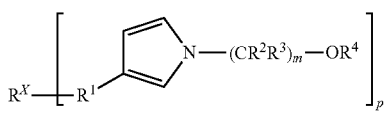

IV to form the compound of formula VII.

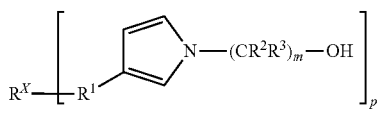

VII

Without being bound or limited to any theory, in some embodiments, the compound of formula V:

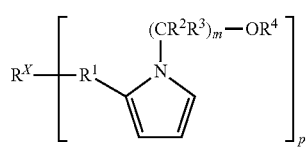

V reacts with the one of more acid(s) of step (c) to form a compound of formula VIII.

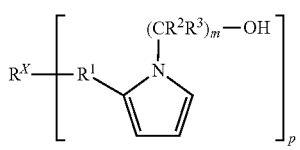

VIII

Without being bound or limited to any theory, in some embodiments, the compound of formula II reacts with the compound of formula VI

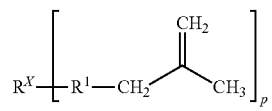

VI in the presence of acid to form the telechelic polymer of formula IV, V, VII, or VII.

Without being bound or limited to any theory, in some embodiments, the compound of formula VIII isomerizes to the compound of formula VII.

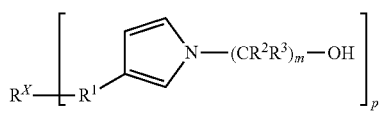

VII

In further embodiments, the compound of formula VIII isomerizes to form the compound of formula VII at a temperature of at least 25° C., at least 30° C., at least 35° C., at least 40° C., at least 45° C., at least 50° C., at least 55° C., at least 60° C., at least 65° C., or at least 70° C.

In some embodiments, the method yields at least 80% of the compound of formula VII, i.e., at least 80% by mole of the compound of formula VII forms relative to all polymer products formed. In some embodiments, the method yields at least 85% of the compound of formula VII. In some embodiments, the method yields at least 90% of the compound of formula VII. In some embodiments, the method yields at least 95% of the compound of formula VII. In some embodiments, the method yields at least 97% of the compound of formula VII. In some embodiments, the method yields at least 98% of the compound of formula VII. In some embodiments, the method yields at least 99% of the compound of formula VII.

In some embodiments, $R^1$ is a divalent polyisobutylene group.

In some embodiments, $R^2$ and $R^3$ are each, independently, H or alkyl from 1 to 3 carbons.

In some embodiments, $R^2$ and $R^3$ are both H.

In some embodiments, m is an integer from 2-10, from 2 to 8, from 2 to 6, from 2 to 4, or from 2 to 3.

In some embodiments, $R^4$ is alkyl, alkenyl, alkynyl, aryl, alkaryl, or aralkyl.

In some embodiments, $R^4$ is alkyl of 1 to 6 carbons, alkenyl of 3 to 6 carbons, alkynyl of 3 to 6 carbons, aryl of 6 to 10 carbons, alkaryl of 7 to 16 carbons, or aralkyl of 7 to 16 carbons.

In some embodiments, $R^4$ is

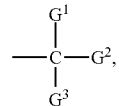

wherein $G^1$ is H or alkyl of 1-3 carbons; and $G^2$ and $G^3$ are each, independently, alkyl of 1-3 carbons.

In some embodiments, $G^1$ is alkyl of 1-3 carbons.

In some embodiments, $R^4$ is isopropyl or tert-butyl.

In some embodiments, $R^1$ is a divalent polyisobutylene group, $R^1$ and $R^2$ are both H, m is 2-3, and $R^4$ is isopropyl or tert-butyl.

In some embodiments, p is 1. In some embodiments, p is 2. In some embodiments, p is 3. In some embodiments, p is 4.

In some embodiments, the telechelic polymer of formula I is a compound of formula VII.

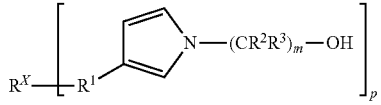

VII

In some embodiments, the telechelic polymer of formula I is a compound of formula VIII.

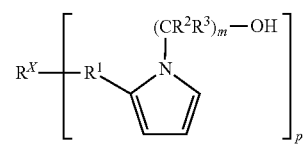

VIII

In some embodiments, p is 1 and $R^X$ is

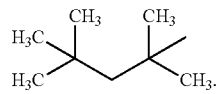

In some embodiments, the telechelic polymer of formula I is a compound of formula IX

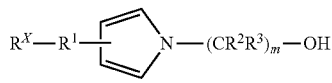

IX wherein $R^X$ is a monovalent cationic residue.

In further embodiments, the telechelic compound of formula I is a compound of formula X.

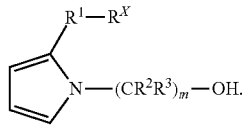

X wherein $R^X$ is a monovalent cationic residue.

In further embodiments, the telechelic compound of formula I is a compound of formula XI.

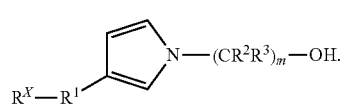

XI wherein $R^X$ is a monovalent cationic residue.

In some embodiments, $R^X$ is

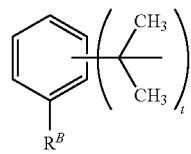

wherein $R^B$ is alkyl and t is an integer from 1-3 and t and p are the same integer.

In some embodiments, the telechelic polymer of formula I is a compound of formula XII:

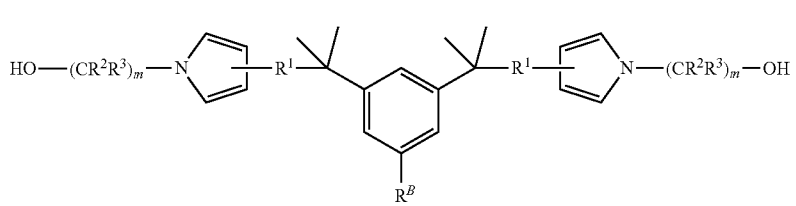

XII wherein $R^B$ is alkyl.

In some embodiments, the telechelic polymer of formula I is a compound of formula XIII.

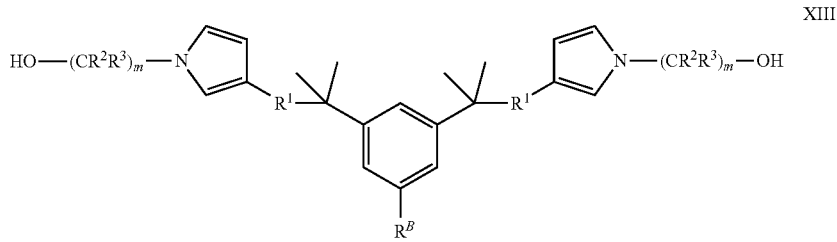

XIII

In some embodiments, the telechelic polymer of formula I is a compound of formula XIV.

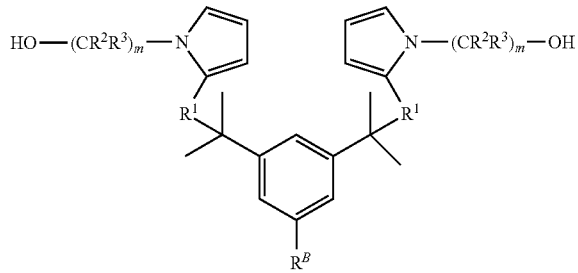

XIV

In some embodiments, the telechlic polymer of formula I is a compound of formula XV.

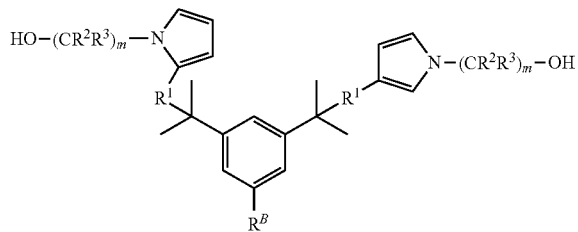

XV

In some embodiments, $R^B$ is alkyl of 1 to 6 carbons. In some embodiments, $R^B$ is tert-butyl.

In some embodiments, the telechelic polymer of formula I has a polydispersity index of from about 1 to about 2, about 1.0 to about 1.5, about 1.0 to about 1.2, or about 1.00 to about 1.10.

In some embodiments, the telechelic polymer of formula I has a number average molecular weight between about $5.0 \times 10^2$ g/mol to about $1.0 \times 10^5$ g/mol.

In some embodiments, the telechelic polymer of formula I has a number average molecular weight between about $1.0 \times 10^3$ g/mol to about $1.0 \times 10^4$ g/mol.

In some embodiments, the telechelic polymer of formula I has a number average molecular weight between about $1.0 \times 10^3$ g/mol and about $5.0 \times 10^3$ g/mol.

In some embodiments, the telechelic polymer of formula I has a number average molecular weight between about $2.0 \times 10^3$ g/mol and about $3.0 \times 10^3$ g/mol.

(i) Generating Quasiliving Carbocationic Polyolefins

Quasiliving carbocationic polyolefins may be generated by methods known to those of ordinary skill in the art. Non-limiting examples of such methods are described in EP 206756 B1 and WO 2006/110647 A1, both of which are incorporated by reference herein.

In some embodiments, a monomer, an initiator, and a Lewis acid are used. In some embodiments, an electron donor, common ion salt, and/or common ion salt precursor is/are used. In some embodiments, the ionized polyolefin is a quasiliving carbocationic polyisobutylene of the following formula:

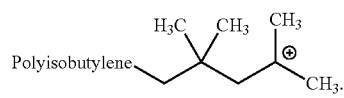

In some embodiments, the quasiliving carbocationic polyolefin is generated from a preformed polyolefin.

Some non-limiting examples of reagents and conditions suitable for polymerizations producing quasiliving polyolefins will be described below.

(A) Initiators

In some embodiments, the initiator is a compound or polyolefin with one, or more than one, end group capable of initiating a cationic olefin polymerization. For example, the initiator can be a compound of formula $(X'—CR_aR_b)_rR_c$, wherein $R_a$ and $R_b$ are independently hydrogen, alkyl, aryl, alkaryl, or aralkyl, provided that at least one of $R_a$ or $R_b$ is not hydrogen; and $R_c$ is an aliphatic or aromatic univalent or polyvalent radical with valence r, wherein r is an integer from one to 4. X' is an acyl, alkoxy, or hydroxy group, or a halogen. In some embodiments, $R_a$, $R_b$ and $R_c$, are hydrocarbon groups containing one carbon atom to about 20 carbon atoms. In some embodiments, $R_a$, $R_b$ and $R_c$, are hydrocarbyl groups containing one carbon atom to about 8 carbon atoms. In some embodiments, X' is a halogen. In some embodiments, X' is chloride. In some embodiments, the structure of $R_a$, $R_b$ and $R_c$, mimics the growing species or monomer. In some embodiments, such structure is a 1-halo-1-tolylethane initiator for polystyrene or a 2-halo-2,4,4-trimethyl pentane initiator for polyisobutylene. In some embodiments, $R_a$, $R_b$ and $R_c$, are each hydrocarbon groups containing one carbon atom to about 10 carbon atoms for the initiation of an isobutylene polymerization. In some embodiments, the initiator is a cumyl, dicumyl or tricumyl halide. In some embodiments, r is 1 or 2.

Some exemplary initiators include 2-chloro-2-phenylpropane, i.e., cumyl chloride; 1,4-di(2-chloro-2-propyl)benzene, i.e., di(cumylchloride); 1,3,5-tri(2-chloro-2-propyl)benzene, i.e., tri(cumylchloride); 2-acetoxy-2-phenylpropane, i.e., cumyl acetate; 2-propionyloxy-2-phenyl propane, i.e., cumyl propionate; 2-methoxy-2-phenylpropane, i.e., cumylmethyl ether; 1,4-di(2-methoxy-2-propyl)benzene, i.e., di(cumylmethyl ether); 1,3,5-tri(2-methoxy-2-propyl)benzene, i.e., tri (cumylmethyl ether); 2-chloro-2,4,4-trimethyl pentane (TMPCl); 2-chloro-2,4,4,6,6-pentamethylheptane (PMHCl); 1,3-di(2-chloro-2-propyl)benzene; 2,6-dichloro-2,4,4,6-tetramethylheptane; and 1,3,-di(2-chloro-2-propyl)-5-tert-butylbenzene (bDCC).

In some embodiments, the initiator is mono-functional, bi-functional, or multi-functional. As used herein, "mono-functional initiator" refers to an initiator that provides approximately one stoichiometric equivalent of carbocation relative to initiator. When a mono-functional initiator is used, the chain-end concentration is approximately equal to the initiator concentration. As used herein, "multi-functional initiator" refers to an initiator that provides approximately x stoichiometric equivalents of carbocation relative to initiator, wherein x represents the functionality of the initiator. When a multi-functional initiator is used, when the functionality of the initiator equals x, then the chain-end concentration is approximately equal to x times the initiator concentration. In some embodiments, x is 2, and the initiator is a bi-functional initiator.

In some embodiments, the mono-functional initiator is 2-chloro-2-phenylpropane, 2-acetoxy-2-phenylpropane, 2-propionyloxy-2-phenylpropane, 2-methoxy-2-phenylpropane, 2-ethoxy-2-phenylpropane, 2-chloro-2,4,4-trimethylpentane, 2-acetoxy-2,4,4,-trimethylpentane, 2-propionyloxy-2,4,4-trimethylpentane, 2-methoxy-2,4,4-trimethylpentane, 2-ethoxy-2,4,4-trimethylpentane, or 2-chloro-2,4,4-trimethylpentane, 2-chloro-2,4,4,6,6-pentamethylheptane, 2-acetoxy-2,4,4,6,6-pentamethylheptane, 2-propionyloxy-2,4,4,6,6-pentamethylheptane, 2-methoxy-2,4,4,6,6-pentamethylheptane, or 2-ethoxy-2,4,4,6,6-pentamethylheptane. In some embodiments, the initiator is 2-chloro-2,4,4-trimethylpentane.

In some embodiments, the bi-functional initiator is 1,3-di(2-chloro-2-propyl)benzene, 1,3-di(2-methoxy-2-propyl)benzene, 1,4-di(2-chloro-2-propyl)benzene, 1,4-di(2-methoxy-2-propyl)benzene, 1,3-di(2-chloro-2-propyl)-5-tert-butylbenzene, 1,3-di(2-methoxy-2-propyl)-5-tert-butylbenzene, 2,6-dichloro-2,4,4,6-tetramethylheptane, or 2,6-dimethoxy-2,4,4,6-tetramethylheptane. In some embodiments, the initiator is 1,3-di(2-chloro-2-propyl)-5-tert-butylbenzene or 2,6-dichloro-2,4,4,6-tetramethylheptane. In some embodiments, the initiator is 1,3-di(2-chloro-2-propyl)-5-tert-butylbenzene.

In some embodiments, the multi-functional initiator is 1,3,5-tri(2-chloro-2-propyl)benzene, 1,3,5-tri(2-bromo-2-propyl)benzene, or 1,3,5-tri(2-methoxy-2-propyl)benzene.

(B) Monomers

In some embodiments, the monomer is a hydrocarbon monomer, i.e., a compound containing only hydrogen and carbon atoms, including but not limited to, olefins and diolefins, and those having from about 2 to about 20 carbon atoms. In some embodiments, such compounds have from about 4 to about 8 carbon atoms.

In some embodiments, the methods described herein can be employed for the polymerization of such monomers to produce polymers of different, but uniform molecular weights. In some embodiments, such molecular weight is from about 300 to in excess of a million g/mol. In some embodiments, such polymers are low molecular weight liquid or viscous polymers having a molecular weight of from about 200 to 10,000 g/mol, or solid waxy to plastic, or elastomeric materials having molecular weights of from about 100,000 to 1,000,000 g/mol, or more.

In some embodiments, the monomer is isobutylene, styrene, beta pinene, isoprene, butadiene, or substituted compounds of the preceding types. In some embodiments, the monomer is isobutylene, 2-methyl-1-butene, 3-methyl-1-butene, 4-methyl-1-pentene, or styrene. In some embodiments, the monomer is isobutylene.

In some embodiments, mixtures of monomers are used.

(C) Lewis Acids

In some embodiments, the Lewis acid is a non-protic acid. In some embodiments, the Lewis acid is a metal halide or non-metal halide. In some embodiments, the Lewis acid is a metal halide. In some embodiments, the Lewis acid is a titanium (IV) halide, a zinc (II) halide, a tin (IV) halide, or an aluminum (III) halide. In some embodiments, the Lewis acid is a titanium(IV) halide. In some embodiments, the Lewis acid is a tin (IV) halide. In some embodiments, the Lewis acid an aluminum (III) halide. In some embodiments, the Lewis acid is titanium tetrabromide or titanium tetrachloride. In some embodiments, the Lewis acid is titanium tetrachloride. In some embodiments, the Lewis acid is zinc chloride. In some embodiments, the Lewis acid is $AlBr_3$. In some embodiments, the Lewis acid is ethyl aluminum dichloride. In some embodiments, the Lewis acid is methyl aluminum dichloride. In some embodiments the Lewis acid is a non-metal halide. In some embodiments, the Lewis acid is an antimony (VI) halide, a gallium (III) halide, or a boron (III) halide. In some embodiments, the Lewis acid is boron trichloride. In some embodiments, the Lewis acid is a trialkyl aluminum compound. In some embodiments, the Lewis acid is trimethyl aluminum.

In some embodiments, one Lewis acid is used. In some embodiments, a mixture of two or more Lewis acids is used. In some embodiments, a mixture of two Lewis acids is used. In some embodiments, a mixture of an aluminum (III) halide and trialkyl aluminum compound is used. In some embodiments, a stoichiometric ratio of about 1:1 aluminum (III) halide to trialkyl aluminum compound is used. In some embodiments, a stoichiometric ratio of 2:1 aluminum (III) halide to trialkyl aluminum compound is used. In some embodiments, a stoichiometric ratio of 1:2 aluminum (III) halide to trialkyl aluminum is used. In some embodiments, the stoichiometric ratio of aluminum (III) halide to trialkyl aluminum is greater than 1. In some embodiments, the stoichiometric ratio of aluminum (III) halide to trialkyl aluminum is less than 1. In some embodiments, a mixture of aluminum trichloride and trimethyl aluminum is used.

In some embodiments, the Lewis acid is a titanium halide, aluminum halide, boron halide, or an alkyl aluminum halide, as defined herein.

In some embodiments, the Lewis acid is an alkyl aluminum halide. In some embodiments, the alkyl is methyl or ethyl. In some embodiments, the halide is Cl or Br.

In some embodiments, the Lewis acid is added in one aliquot. In some embodiments, the Lewis acid is added in more than one aliquot. In some embodiments, the Lewis acid is added in two aliquots. In some embodiments, a first aliquot of Lewis acid is added during the polymerization reaction, and a second aliquot of Lewis acid is added after the addition of the compounds of formula II.

(D) Electron Donors

As is understood to one of ordinary skill in the art, some electron donors are capable of converting traditional polymerization systems into quasiliving carbocationic polymerization systems. In some embodiments, the methods described herein are performed in the presence of an electron donor.

In some embodiments, the electron donor is capable of complexing with Lewis acids. In some embodiments, the electron donor is a base and/or nucleophile. In some embodiments, the electron donor is capable of abstracting or removing a proton. In some embodiments, the electron donor is an organic base. In some embodiments, the electron donor is an amide. In some embodiments, the electron donor is N,N-dimethylformamide, N,N-dimethylacetamide, or N,N-diethylacetamide. In some embodiments, the electron donor is a sulfoxide. In some embodiments, the electron donor is dimethyl sulfoxide. In some embodiments, the electron donor is an ester. In some embodiments, the electron donor is methyl acetate or ethyl acetate. In some embodiments, the electron donor is a phosphate compound. In some embodiments, the electron donor is trimethyl phosphate, tributyl phosphate, or triamide hexamethylphosphate. In some embodiments, the electron donor is an oxygen-containing metal compound. In some embodiments, the electron donor is tetraisopropyl titanate.

In some embodiments, the electron donor is pyridine or a pyridine derivative. In some embodiments, the electron donor is a compound of formula:

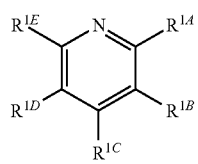

wherein $R^{1A}$, $R^{1B}$, $R^{1C}$, $R^{1D}$, and $R^{1E}$ are each, independently, hydrogen or hydrocarbyl; or $R^{1A}$ and $R^{1B}$, or $R^{1B}$ and $R^{1C}$, or $R^{1C}$ and $R^{1D}$, or $R^{1D}$ and $R^{1E}$ independently form a fused aliphatic ring of about 3 to about 7 carbon atoms or a fused aromatic ring of about 5 to about 7 carbon atoms. In some embodiments, $R^{1A}$ and $R^{1E}$ are each, independently, hydrocarbyl, and $R^{1B}$-$R^{1D}$ are hydrogen.

In some embodiments, the electron donor is 2,6-di-tert-butylpyridine, 2,6-lutidine, 2,4-lutidine, 2,4,6-trimethylpyridine, 2-methylpyridine, or pyridine. In some embodiments, the electron donor is N,N-dimethylaniline or N,N-dimethyltoluidine. In some embodiments, the electron donor is 2,6-lutidine.

(E) Common Ion Salts and Ion Salt Precursors

In some embodiments, common ion salts or salt precursors may be optionally added to the reaction mixture in addition to or in replacement of the electron donor. In some embodiments, such salts may be used to increase the ionic strength, suppress free ions, and interact with ligand exchange. In some embodiments, the common ion salt precursor is tetra-n-butylammonium chloride. In some embodiments, the common ion salt precursor is tetra-n-butylammonium bromide. In some embodiments, the common ion salt precursor is tetra-n-butylammonium iodide. In some embodiments, the concentration of the common ion salts or salt precursors in the total reaction mixture may be in the range from about 0.0005 moles per liter to about 0.05 moles per liter. In some embodiments, the concentration of the common ion salts or salt precursors is in the range from about 0.0005 moles per liter to about 0.025 moles per liter. In some embodiments, the concentration of the common ion salt or salt precursors is in the range from about 0.001 moles per liter to about 0.007 moles per liter.

(F) Quenching Agents and Quenching Time

In some embodiments, a quasiliving carbocationic polyolefin is generated, and after polymerization proceeds for a desired time, the quasiliving carbocationic polyolefin is quenched with a compound of formula II

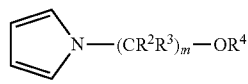

II wherein $R^4$ is alkyl, alkenyl, alkynyl, aryl, alkaryl, aralkyl, —C(O)$R^5$; —SO$_3$$R^6$, —SO$_2$$R^7$, —Si($R^8$)($R^9$)($R^{10}$) wherein $R^5$, $R^6$, $R^7$, $R^8$, $R^9$, and $R^{10}$ are each independently, alkyl or aryl.

In some embodiments, $R^4$ is alkyl, alkenyl, alkynyl, aryl, alkaryl, or aralkyl.

In some embodiments, $R^4$ is alkyl of 1 to 6 carbons, alkenyl of 3 to 6 carbons, alkynyl of 3 to 6 carbons, aryl of 6 to 10 carbons, alkaryl of 7 to 16 carbons, or aralkyl of 7 to 16 carbons.

In some embodiments, $R^4$ is

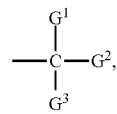

wherein $G^1$ is H or alkyl of 1-3 carbons; and $G^2$ and $G^3$ are each, independently, alkyl of 1-3 carbons.

In some embodiments, $G^1$ is alkyl of 1-3 carbons.
In some embodiments, $R^4$ is isopropyl or tert-butyl.
In some embodiments, step (b) is performed for about 5 minutes to about 120 minutes. In some embodiments, step (b) is performed for about 15 minutes to about 90 minutes. In some embodiments, step (b) is perform for about 30 minutes to about 60 minutes.

In some embodiments, prior to step (b), the quasiliving reaction system of step (a) is terminated and subsequently reactivated zero, one, or more times at a desired time. In some embodiments, the quasiliving reaction system of step (a) is terminated and subsequently reactivated zero times, i.e., after generation of the quasiliving carbocationic polyolefin of step (a), the quasiliving reaction system of step (a) is not terminated at any time prior to step (b). In some embodiments, the quasiliving reaction system of step (a) is terminated and subsequently reactivated one time.

In some embodiments, the compound of formula II is added after high conversion of the monomer. In particular embodiments, the compound of formula II is added after 80%, 85%, 90%, 95%, 97%, 99%, or 99.9% of the monomer has been polymerized into the quasiliving carbocationic polyolefin.

(G) Temperature

In some embodiments, steps (a) and (b) are performed at a temperature from about −120° C. to about 0° C. In some embodiments, steps (a) and (b) are performed at a temperature from about −110° C. to about −10° C. In some embodiments, steps (a) and (b) are performed at a temperature from about −100° C. to about −20° C. In some embodiments, steps (a) and (b) are performed at a temperature from about −90° C. to about −30° C. In some embodiments, steps (a) and (b) are performed at a temperature from about −80° C. to about −40° C. In some embodiments, steps (a) and (b) are performed at a temperature from about −70° C. to about −40° C. In some embodiments, steps (a) and (b) are performed at a temperature from about −60° C. to about −40° C. In some embodiments, steps (a) and (b) are performed at a temperature of about −40° C., −50° C., −60° C., −70° C., or −80° C. In some embodiments, steps (a) and (b) are performed at a temperature of about −40° C. In some embodiments, steps (a) and (b) are performed at a temperature of about −50° C. In some embodiments, steps (a) and (b) are performed at a temperature of about −60° C. In some embodiments, steps (a) and (b) are performed at a temperature of about −70° C. In some embodiments, steps (a) and (b) are performed at a temperature of about −80° C.

(H) Concentrations

The chain end concentration of the methods described herein is not limited by the disclosed examples. The chain end concentration for the methods described herein appears to have no definite upper limit, and the methods described herein may be performed at any chain end concentration, subject to the inherent limits imposed by the density and molecular weight (i.e., molar volume) of the reaction components.

In some embodiments, the molar concentration of the compounds of formula II is from about 1 to about 10 times the molar concentration of chain ends. In some embodiments, the molar concentration of the compounds of formula II is from about 1.1 to about 8 times the molar concentration of chain ends. In some embodiments, the molar concentration of the compounds of formula II is from about 1.1 to about 5 times the molar concentration of chain ends. In some embodiments, the molar concentration of the compounds of formula II is from about 1.1 to about 4 times the molar concentration of chain ends. In some embodiments, the molar concentration of the compounds of formula II is from about 1.1 to about 3 times the molar concentration of chain ends. In some embodiments, the molar concentration of the compounds of formula II is from about 1.1 to about 2 times the molar concentration of chain ends.

In some embodiments, the molar concentration of Lewis acid is from about 0.5 to about 20 times the molar concentration of chain ends. In some embodiments, the molar concentration of Lewis acid is from about 0.5 to about 15 times the molar concentration of chain ends. In some embodiments, the molar concentration of Lewis acid is from about 1.0 to about 10 times the molar concentration of chain ends. In some embodiments, the molar concentration of Lewis acid is from about 1.0 to about 8 times the molar concentration of chain ends. In some embodiments, the molar concentration of Lewis acid is from about 2 to about 5 times the molar concentration of chain ends.

In some embodiments, the electron donor concentration is less than half the concentration of Lewis acid. In some embodiments, the electron donor concentration is less than 0.4 times the Lewis acid concentration. In some embodiments, the electron donor concentration is less than 0.3 times the Lewis acid concentration. In some embodiments, the electron donor concentration is less than 0.2 times the Lewis acid concentration. In some embodiments, the electron donor concentration is less than 0.1 times the Lewis acid concentration.

In some embodiments, the chain end concentration is less than 0.010 M. In some embodiments, the chain end concentration is less than 0.050 M. In some embodiments, the chain end concentration is less than 0.10 M. In some embodiments, the chain end concentration is less than 0.5 M. In some embodiments, the chain end concentration is less than 1.0 M. In some embodiments, the chain end concentration is greater than 0.001 M.

(ii) In Situ Deblocking with Acid (A) Acids

In some embodiments, the one or more acids of step (c) is a Lewis acid or mixture of Lewis acids.

In some embodiments, the Lewis acid is a non-protic acid. In some embodiments, the Lewis acid is a metal halide or non-metal halide. In some embodiments, the Lewis acid is a metal halide. In some embodiments, the Lewis acid is a titanium (IV) halide, a zinc (II) halide, a tin (IV) halide, or an aluminum (III) halide. In some embodiments, the Lewis acid is a titanium (IV) halide. In some embodiments, the Lewis acid is a tin (IV) halide. In some embodiments, the Lewis acid an aluminum (III) halide. In some embodiments, the Lewis acid is titanium tetrabromide or titanium tetrachloride. In some embodiments, the Lewis acid is titanium tetrachloride. In some embodiments, the Lewis acid is zinc chloride. In some embodiments, the Lewis acid is $AlBr_3$. In some embodiments, the Lewis acid is ethyl aluminum dichloride. In some embodiments, the Lewis acid is methyl aluminum dichloride. In some embodiments the Lewis acid is a non-metal halide. In some embodiments, the Lewis acid is an antimony (VI) halide, a gallium (III) halide, or a boron (III) halide. In some embodiments, the Lewis acid is boron trichloride. In some embodiments, the Lewis acid is a trialkyl aluminum compound. In some embodiments, the Lewis acid is trimethyl aluminum.

In some embodiments, one Lewis acid is used. In some embodiments, a mixture of two or more Lewis acids is used. In some embodiments, a mixture of two Lewis acids is used. In some embodiments, a mixture of an aluminum (III) halide and trialkyl aluminum compound is used. In some embodiments, a stoichiometric ratio of about 1:1 aluminum (III) halide to trialkyl aluminum compound is used. In some embodiments, a stoichiometric ratio of 2:1 aluminum (III) halide to trialkyl aluminum compound is used. In some embodiments, a stoichiometric ratio of about 1:2 aluminum (III) halide to trialkyl aluminum is used. In some embodiments, the stoichiometric ratio of aluminum (III) halide to trialkyl aluminum is greater than 1. In some embodiments, the stoichiometric ratio of aluminum (III) halide to trialkyl aluminum is less than 1. In some embodiments, a mixture of aluminum trichloride and trimethyl aluminum is used.

In some embodiments, the Lewis acid is an alkyl aluminum halide, as defined herein. In some embodiments, the Lewis acid is a methyl aluminum bromide.

In a particular embodiment, the one or more acid(s) of step (c) is a titanium halide, aluminum halide, boron halide, or an alkyl aluminum halide.

In a particular embodiment, the one or more acid(s) of step (c) is titanium tetrachloride, titanium tetrabromide, or an alkyl aluminum chloride or mixture of alkyl aluminum chlorides of the formula $R_nAlX_{3-n}$, wherein n is 1, 1,5, or 2, R is methyl or ethyl, and X is chloride.

In a particular embodiment, at least two acids are used in step (c), and wherein at least one of said at least two acids is ethyl aluminum dichloride and one of said at least two acids is titanium tetrachloride.

In a particular embodiment, at least two acids are used, wherein at least one of said at least two acids is a Lewis acid and one of said at least two acids is a Bronsted acid.

In a particular embodiment, the Bronsted acid is such that its conjugate base does not significantly diminish the activity of the Lewis acid.

In particular embodiments, the Bronsted acid is a carboxylic acid, mineral acid, sulfonic acid, or phosphoric acid. In some embodiments, the carboxylic acid is formic acid, acetic acid, or propionic acid. In some embodiments, the mineral acid is a hydrogen halide. In some embodiments, the hydrogen halide is HF, HCl, HBr, or HI. In some embodiments, the mineral acid is sulfuric acid, phosphoric acid, perchloric acid, or nitric acid. In some embodiments, the sulfonic acid is p-toluenesulfonic acid, trifluoromethane sulfonic acid, or fluorosulfonic acid. In some embodiments, the phosphonic acid is methane phosphonic acid.

In particular embodiments, the Bronsted acid is sulfuric acid, hydrochloric acid, hydrobromic acid, or p-toluenesulfonic acid.

In particular embodiments, at least three acids are used, wherein at least one of said at least three acids is titanium tetrachloride, one of said at least three acids is ethyl aluminum dichloride, and one of said at least three acids is sulfuric acid.

(B) Temperature

In some embodiments, step (c) is performed at a temperature of from about −75° C. to about 80° C.

In some embodiments, the temperature is at least 25° C., at least 30° C., at least 35° C., at least 40° C., at least 45° C., at least 50° C., at least 55° C., at least 60° C., at least 65° C., or at least 70° C. before, during, and/or after the addition of the one or more acid(s) of step (c).

In some embodiments, step (c) is performed initially at a temperature of from about −75° C. to about −55° C. and said temperature is subsequently raised to from about 65° C. to about 85° C. As used herein, "performed initially . . . and subsequently raised," as used in connection with step (c), means that the addition of the one or more acid(s) of step (c) is first performed at the indicated initial temperature; the temperature is then subsequently raised to the indicated temperature at any time after addition of the one or more acid(s) has started. The temperature may be raised to the indicated temperature at any rate.

In some embodiments, step (c) is performed initially at a temperature of about −60° C. and said temperature is subsequently raised to about 70° C. In particular embodiments, the step (c) is performed initially at about −60° C. and allowed to warm to about 25° C. over 30 minutes to 120 minutes; and then heated to about 60-80° C. and maintained about 60-80° C. over 2-6 hours.

(C) Concentrations

In some embodiments, the one or more acid(s) of step (c) includes one or more Lewis acid(s), wherein from about 0.2 to about 20 equivalents of the one or more Lewis acid(s) are present relative to chain ends.

In some embodiments, the one or more acid(s) of step (c) includes one or more Lewis acid(s), wherein from about 0.1 to about 10 equivalents of the one or more Lewis acid(s) are present relative to chain ends.

In some embodiments, the one or more acid(s) of step (c) includes one or more Lewis acid(s), wherein from about 1 to about 5 equivalents of the one or more Lewis acid(s) are present relative to chain ends.

In some embodiments, the one or more acid(s) of step (c) includes one or more Bronsted acid(s), wherein from about 0.001 to about 20 equivalents of the one or more Bronsted acid(s) are present relative to chain ends.

In some embodiments, the one or more acid(s) of step (c) includes one or more Bronsted acid(s), wherein from about 0.1 to about 10 equivalents of the one or more Bronsted acid(s) are present relative to chain ends.

In some embodiments, the one or more acid(s) of step (c) includes one or more Bronsted acid(s), wherein from about 0.5 to about 5 equivalents of the one or more Bronsted acid(s) are present relative to chain ends.

(D) Reaction Time

In some embodiments, step (c) is performed for about 15 minutes to about 8 hours. In some embodiments, step (c) is performed from about 2 to about 6 hours.

In some embodiments, the one or more acids of step (c) contains an alkyl aluminum halide, step (c) is performed initially at about −60° C. and the temperature is subsequently raised to about −10° C., and step (c) is performed for about 30 minutes to about 1 hour.

In some embodiments, the one or more acids of step (c) contains a titanium halide and a Bronsted acid, step (c) is performed initially at about −60° C. and the temperature is subsequently raised to about 5° C., and step (c) is performed for about 30 minutes to about 2 hours.

In some embodiments, the one or more acids of step (c) contains a titanium halide, step (c) is performed initially at about −60° C. and the temperature is raised to about 70° C., and step (c) is performed for about 30 minutes to about 6 hours.

(iii) Diluents

In some embodiments of the methods described herein, the methods are performed in a diluent. In some embodiments, the diluent is a single compound or a mixture of two or more compounds. In some embodiments, the diluent completely dissolves the reaction components or partially dissolves the reaction components. In some embodiments, the diluent completely or nearly completely dissolves the reaction components. In some embodiments, the diluent completely dissolves the reaction components. In some embodiments, the diluent nearly completely dissolves the reaction components.

In some embodiments, the diluent has a low boiling point and/or low freezing point. In some embodiments, the diluent is an alkane. In some embodiments, the diluent is a normal alkane. In some embodiments, the diluent is propane, normal butane, normal pentane, normal hexane, normal heptane, normal octane, normal nonane or normal decane. In some embodiments, the diluent is normal hexane or normal pentane. In some embodiments, the diluent is normal hexane. In some embodiments, the diluent is a branched alkane. In some embodiments, the alkane is isobutane, isopentane, neopentane, isohexane, 3-methylpentane, 2,2-dimethylbutane, or 2,3-dimethylbutane. In some embodiments, the alkane is cyclic. In some embodiments, the alkane is methylcyclohexane. In some embodiments, the diluent is a mixed boiling fraction alkane. In some embodiments, the diluent is a mixed boiling fraction of C5 alkanes, i.e., mixed pentanes or mixed boiling fraction of C6 alkanes, i.e., mixed hexanes. In some embodiments, the alkane is a nitroalkane.

In some embodiments, the diluent is an alkyl halide. In some embodiments, the diluent is an alkyl monohalide or an alkyl polyhalide. In some embodiments, the diluent is chloroform, ethylchloride, n-butyl chloride, methylene chloride, methyl chloride, 1,2-dichloroethane, 1,1,2,2-tetrachloroethane, carbon tetrachloride, 1,1-dichloroethane, n-propyl chloride, isopropyl chloride, 1,2-dichloropropane, or 1,3-dichloropropane. In some embodiments, the diluent is methylene chloride or methyl chloride. In some embodiments, the diluent is methyl chloride. In some embodiments, the diluent is an alkene or halogenated alkene. In some embodiments, the diluent is vinyl chloride, 1,1-dichloroethene, or 1,2-dichloroethene.

In some embodiments, the diluent is a substituted benzene. In some embodiments, the diluent is benzene. In some embodiments, the diluent is toluene.

In some embodiments, the diluent is carbon disulfide, sulfur dioxide, acetic anhydride, acetonitrile, benzene, toluene, ethylbenzene, methylcyclohexane, chlorobenzene, or a nitroalkane.

In some embodiments, the diluent is a mixture of two or more compounds. In some embodiments, the diluent is a mixture of hexane and methyl chloride. In further embodiments, such mixture is from about 10/90 to about 90/10 hexane/methyl chloride by volume. In further embodiments, such mixture is from about 20/80 to about 80/20 hexane/methyl chloride by volume. In further embodiments, such mixture is from about 30/70 to about 70/30 hexane/methyl chloride by volume. In further embodiments, such mixture is from about 40/60 to about 60/40 hexane/methyl chloride by volume. In further embodiments, such mixture is about 50/50 hexane/methyl chloride by volume. In further embodiments, such mixture is about 60/40 hexane/methyl chloride by volume. In further embodiments, such mixture is about 40/60 hexane/methyl chloride by volume.

(iv) Terminators

In some embodiments, the terminator is a compound capable of deactivating a Lewis acid. In some embodiments, the terminator is a base and/or a nucleophile. In some embodiments, the terminator is a base. In some embodiments, the terminator is an electron donor. In some embodiments, the terminator is an organic base. In some embodiments, the terminator is an alcohol or amine. In some embodiments, the terminator is an alcohol. In some embodiments, the terminator is a pyridine derivative.

In some embodiments, the terminator is methanol, ethanol, or isopropanol. In some embodiments, the terminator is methanol. In some embodiments, the terminator is water. In some embodiments, the terminator is diethylamine, triethylamine, pyridine, 2,6-lutidine, n-butylamine, or tert-amylamine.

In some embodiments, the terminator is added after step (c).

(C) Compositions of Matter

In some embodiments, provided herein are compounds of formula I:

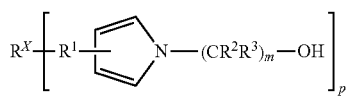

wherein:
- $R^1$ is a polyolefin group;
- $R^2$ and $R^3$ are, independently in each —$(CR^2R^3)$— unit, hydrogen or alkyl from 1 to 6 carbons;
- m is an integer from 2 to 20;
- $R^X$ is a cationic initiator residue; and
- p is an integer from 1 to 4.

In some embodiments, $R^1$ is in the 3-position of the pyrrole ring.

In some embodiments, $R^1$ is in the 2-position of the pyrrole ring.

In some embodiments, $R^1$ is a polyisobutylene group.

In some embodiments, $R^2$ and $R^3$ are each, independently, H or alkyl from 1 to 3 carbons.

In some embodiments, $R^2$ and $R^3$ are hydrogen.

In some embodiments, m is an integer from 2-10, from 2 to 8, from 2 to 6, from 2 to 4, or from 2 to 3.

In some embodiments, p is 1. In some embodiments, p is 2. In some embodiments, p is 3. In some embodiments, p is 4.

In some embodiments, the compound of formula I is a compound of formula VII.

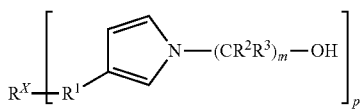

In some embodiments, the compound of formula I is a compound of formula VIII.

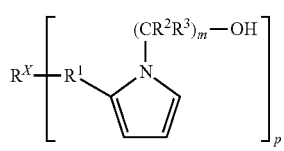

In some embodiments, p is 1 and $R^X$ is

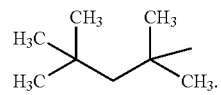

In some embodiments, the compound of formula I is a compound of formula IX

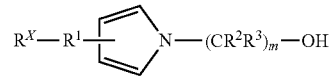

wherein $R^X$ is a monovalent cationic residue.

In further embodiments, the compound of formula I is a compound of formula X.

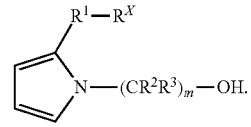

wherein $R^X$ is a monovalent cationic residue.

In further embodiments, the compound of formula I is a compound of formula XI

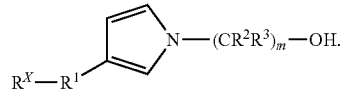

wherein $R^X$ is a monovalent cationic residue.

In some embodiments, $R^X$ is

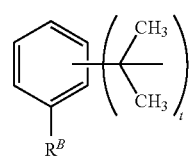

wherein $R^B$ is alkyl and t is an integer from 1-3 and t and p are the same integer.

In some embodiments, the compound of formula I is a compound of formula XII

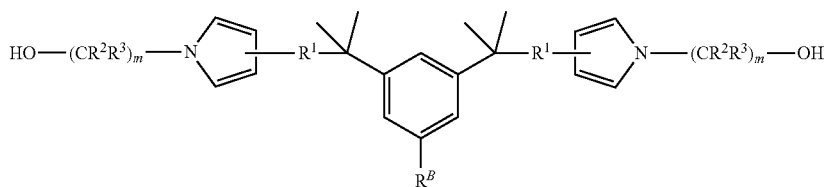

XII wherein $R^B$ is alkyl.

In some embodiments, the compound of formula I is a compound of formula XIII.

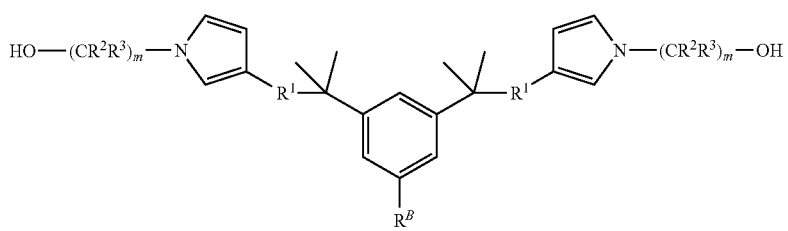

XIII

In some embodiments, the compound of formula I is a compound of formula IX.

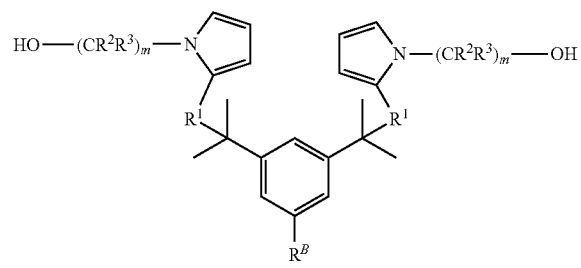

XIV

In some embodiments, the compound of formula I is a compound of formula XV.

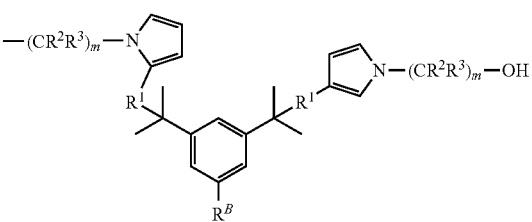

XV

In some embodiments, $R^B$ is alkyl of 1 to 6 carbons. In some embodiments, $R^B$ is tert-butyl.

In some embodiments, the compound of formula I has a polydispersity index of from about 1 to about 2, about 1.0 to about 1.5, about 1.0 to about 1.2, or about 1.00 to about 1.10.

In some embodiments, the compound of formula I has a number average molecular weight between about $5.0 \times 10^2$ g/mol to about $1.0 \times 10^5$ g/mol.

In some embodiments, the compound of formula I has a number average molecular weight between about $1.0 \times 10^3$ g/mol to about $1.0 \times 10^4$ g/mol.

In some embodiments, the compound of formula I has a number average molecular weight between about $1.0 \times 10^3$ g/mol and about $5.0 \times 10^3$ g/mol.

In some embodiments, the compound of formula I has a number average molecular weight between about $2.0 \times 10^3$ g/mol and about $3.0 \times 10^3$ g/mol.

The embodiments and examples described above and the examples that follow are intended to be merely exemplary, and such examples and embodiments are non-limiting. For example, included within the scope of the subject matter described herein are all combinations of the embodiments described herein. In addition, one of ordinary skill in the art will recognize, or will be able to ascertain using no more than routine experimentation, modifications of the embodiments and examples described herein. Such modifications are considered to be within the scope of the claimed subject matter and are encompassed by the appended claims.

(c) Examples (i) Example 1

This example involves capping of quasiliving monofunctional polyisobutylene with N-(2-tert-butoxy-ethyl)pyrrole to obtain hydroxyl chain ends in situ.

Under a $N_2$ atmosphere, 105-mL of hexane and 70-mL of methyl chloride were chilled to −60° C. and placed in a 4-neck round bottom flask equipped with an overhead stirrer, thermocouple, and ReactIR probe. To the 60/40 (v/v) mixture of hexane and methyl chloride, were added 0.109-mL of 2,6-dimethylpyridine and 0.648 mL of 2-chloro-2,4,4-trimethylpentane (TMPCl) providing a proton trap concentration of 0.005 M and a chain end concentration of 0.02 M. A final molecular weight of 2,000 g/mol was targeted by charging the reactor with 9.9 mL of isobutylene. After thermal equilibration, the polymerization was initiated with 1.26 mL (3 eq.) of $TiCl_4$. Upon complete monomer conversion, 2 mL (3 eq.) of N-(2-tert-butoxyethyl)pyrrole was added, and the alkylation reaction was allowed to proceed for approximately 50 min. The reactor was then charged with 2 mL (5 eq.) of ethyl aluminum dichloride and 0.4 mL (2 eq.) of sulfuric acid to promote removal of the terminal tert-butyl blocking group residing on the pyrrole capping agent. After addition of the acids, the reaction flask was immediately removed from the cooling bath and allowed to warm at ambient temperature for 90 min. At this point, a majority of the methyl chloride had boiled off, and the reaction flask was placed on a heating mantle and heated to reflux (69° C.) for 3 h. Finally, the catalysts were destroyed by addition of methanol.

Initial alkylation of N-(2-tert-butoxyethyl)pyrrole resulted in 57% of the C-3 alkylated isomer, 38% of the C-2 alkylated isomer, and 5% exo-olefin chain ends. Addition of the ethyl aluminum dichloride and sulfuric acid with subsequent heating resulted in reaction of the exo-olefin chain ends with excess N-(2-tert-butoxyethyl)pyrrole, complete displacement of the terminal tert-butyl groups to yield terminal hydroxyl groups, and isomerization of the chain ends to provide 99% of the C-3 alkylated isomer and 1% of the C-2 alkylated isomer. The final hydroxy functional polymer had a number average molecular weight (polydispersity) of 2,056 g/mol (1.05).

(ii) Example 2

This example involved capping of quasi-living difunctional polyisobutylene with N-(2-tert-butoxy-ethyl)pyrrole to obtain hydroxyl chain ends in situ.

Under a $N_2$ atmosphere, 105-mL of hexane and 70-mL of methyl chloride were chilled to −60° C. and placed in a 4-neck round bottom flask equipped with an overhead stirrer, thermocouple, and ReactIR probe. To the 60/40 (v/v) mixture of hexane and methyl chloride, were added 0.109-mL of 2,6-dimethylpyridine and 0.54 g of 1,3-bis(2-chloro-2-propyl)-5-tert-butylbenzene (bDCC) providing a proton trap concentration of 0.005 M and a chain end concentration of 0.02 M. A final molecular weight of 3000 g/mol was targeted by charging the reactor with 7.03 mL of isobutylene. After thermal equilibration, the polymerization was initiated with 1.26 mL (3 eq.) of $TiCl_4$. Upon complete monomer conversion, 2 mL (3 eq.) of N-(2-tert-butoxyethyl)pyrrole was added, and the alkylation reaction was allowed to proceed for approximately 30 min. The reactor was then charged with 2 mL (5 eq.) of ethyl aluminum dichloride and 0.4 mL (2 eq.) of sulfuric acid to promote removal of the terminal tert-butyl blocking group residing on the pyrrole capping agent. After addition of the acids, the reaction flask was immediately removed from the cooling bath and allowed to warm at ambient temperature for 90 min. At this point, a majority of the methyl chloride had boiled off, and the reaction flask was placed on a heating mantle and heated to reflux (69° C.) for 4 h. Finally, the catalysts were destroyed by addition of methanol.

Initial alkylation of N-(2-tert-butoxyethyl)pyrrole resulted in 55% of the C-3 alkylated isomer, 38% of the C-2 alkylated isomer, 5% exo-olefin chain ends, and 2% coupling through double alkylation of pyrrole. Addition of the ethyl aluminum dichloride and sulfuric acid with subsequent heating resulted in reaction of the exo-olefin chain ends with excess N-(2-tert-butoxyethyl)pyrrole, complete displacement of the terminal tert-butyl groups to yield terminal hydroxyl groups, and isomerization of the chain ends to provide 98% of the C-3 alkylated isomer and 2% of coupled chain ends. The final hydroxy functional polymer had a number average molecular weight (polydispersity) of 3084 g/mol (1.05).

(iii) Example 3

The following was conducted under a dry, $N_2$ atmosphere. Into a 60/40 (v/v) mixture of hexane (105 mL) and methyl chloride (70 mL) at −60° C. were dissolved 6.9 g of 2,000 g/mol tert-chloride terminated polyisobutylene, 0.11 mL of 2,6-lutidine, and 1.9 mL (3 eq) of N-(2-tert-butoxyethyl) pyrrole. The alkylation reaction was initiated with the addition of 1.19 mL (3 eq) of $TiCl_4$. After 30-min of reaction time, additional acids were charged to the reactor, and it was immediately removed from the cooling bath and allowed to warm at ambient temperature to promote removal of the terminal tert-butyl group. The reactor was vented during warming to allow volatilization of methyl chloride.

Four separate reactions were performed using the following combinations of additional acids for deblocking: A) 5 eq of $TiCl_4$, B) 5 eq of $TiCl_4$ and 2 eq of $H_2SO_4$, C) 5 eq of $EtAlCl_2$, and D) 5 eq of $EtAlCl_2$ and 2 eq of $H_2SO_4$. After less than 30 min warming at ambient temperature, combination D) resulted in complete displacement of the terminal tert-butyl groups to yield 92% hydroxyl and 8% residual exo-olefin functionality. Similarly, combination C) resulted in complete displacement of the terminal tert-butyl groups in less than 30 min to yield 96% hydroxyl and 4% residual exo-olefin functionality. Combination B) required less than 90 min for complete deblocking, yielding 91% hydroxyl functionality and 3% residual tert-chloride chain ends; the remaining 6% of the chains were coupled through double alkylation of single pyrrole moieties (C-2 and C-4). Combination A) provided only 49% deblocking after 4.5 h with 4% exo-olefin, 7% chain coupling; for the remaining 40% of the chains the terminal tert-buyl group stayed intact.

After 4.5 h, the remaining contents of each reactor, i.e. the polymer in hexane with the acids, was heated to reflux (69° C.) under $N_2$ for an additional 3.5 h. After heating, condition A) provided 83% hydroxyl functionality with 5% residual exo-olefin. Chain coupling through the pyrrole chain end was also increased to 12%. Heating combination B) resulted in a slight decrease in hydroxyl functionality to 89% and an increase in coupling to 9% with 2% residual exo-olefin. Heating combination D) induced further alkylation of pyrrole with the exo-olefin terminated polyisobutylene to provide 100% hydroxyl functionality. Heating combination C) did not induce further alkylation of pyrrole or chain coupling. However, for all four conditions, heating for 3.5 h induced isomerization; the C-2 alkylated pyrrole isomers were converted to the more thermodynamically stable C-3 alkylated pyrrole isomers.

(iv) Example 4

This example involves hydroxy-terminated polyisobutylene obtained by quasiliving isobutylene polymerization and quenching with N-(2-tert-butoxyethyl)pyrrole using only dimethyl aluminum chloride catalysis.

A stirred glass reactor was cooled to −75° C. within a $N_2$-atmosphere glovebox. To the reactor were charged 120 mL of a 50/50 (v/v) mixture of methyl chloride/hexane, 0.45 mL of 2-chloro-2,4,4-trimethylpentane, 0.08 mL of 2,6-lutidine, and 6.76 mL of isobutylene. The (initiator) chain end concentration was 0.02 M, 2,6-lutidine was present at a concentration 0.005 M, and a molecular weight of 2,000 g/mol was targeted. The polymerization was initiated with the addition of 2.64 mL (6 eq per chain end) of a 1 M solution of dimethyl aluminum chloride in hexane. Full monomer conversion was reached in approximately 2.5 h, and a reaction aliquot at that point indicated tert-chloride chain end functionality. The reaction was quenched by addition of 1.4 mL of N-(2-tert-butoxyethyl)pyrrole to the reactor (3 eq per chain end), and after 1.5 h the reactor was removed from the cooling bath and allowed to sit under a $N_2$ atmosphere at room temperature overnight (19 h) before destroying the catalyst with excess methanol. Analysis of the final polyisobutylene indicated near quantitative primary hydroxyl chain end functionality (>98% and a C-3/C-2 isomer ratio of 62/38) with <2% residual olefin end groups).

(v) Example 5

This example involves hydroxy-terminated polyisobutylene obtained by boron trichloride (BCl$_3$)-catalyzed quasiliving isobutylene polymerization and subsequent dimethyl aluminum chloride-catalyzed alkylation of N-(2-tert-butoxyethyl)pyrrole.

A stirred glass reactor was cooled to –60° C. within a N$_2$-atmosphere glovebox. To the reactor were charged 175 mL of methyl chloride, 0.68 mL of 2-chloro-2,4,4-trimethylpentane, and 0.1 mL of 2,6-lutidine. Polymerization was initiated by addition of 7.4 mL (24 eq per chain end) BCl$_3$. The (initiator) chain end concentration was 0.02 M, and a molecular weight of 2,000 g/mol was targeted. Complete monomer conversion was achieved in 6.6 h. A prequench aliquot indicated perfect tert-chloride chain end functionality. The polymerization was quenched by addition of 1.4 mL of N-(2-tert-butoxyethyl)pyrrole (2 eq per chain end) along with 2.64 mL (6 eq per chain end) of a 1 M dimethyl aluminum chloride solution in hexane. After 2.5 h, a reaction aliquot indicated quantitative capping by the pyrrole quencher (C-3/C-2 isomer ratio of 63/35) and cleavage of the terminal tert-butyl ether to provide hydroxyl functionality at the chain end.

What is claimed is:

1. A compound of formula I:

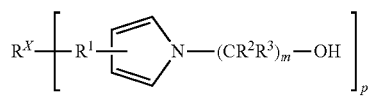

wherein:
R$^1$ is a divalent polyolefin group;
R$^2$ and R$^3$ are, independently in each —(CR$^2$R$^3$)— unit, hydrogen or alkyl from 1 to 6 carbons;
m is an integer from 2 to 20;
R$^X$ is a cationic initiator residue; and
p is an integer from 1 to 4.

2. The compound of claim 1, wherein R$^1$ is in the 3-position of the pyrrole ring.

3. The compound of claim 1, wherein R$^1$ is in the 2-position of the pyrrole ring.

4. The compound of claim 1, wherein R$^1$ is a divalent polyisobutylene group.

5. The compound of claim 1, wherein R$^2$ and R$^3$ are hydrogen.

6. The compound of claim 1, wherein m is 2 or 3.

7. The compound of claim 1, wherein p is 1 and R$^X$ is

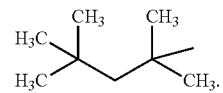

8. The compound of claim 1, wherein the R$^X$ is:

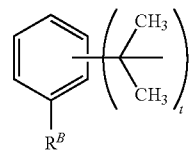

wherein R$^B$ is alkyl; t is an integer from 1-3; and t and p are the same integer.

9. The compound of claim 1, wherein the compound of formula I is the compound of formula XIII:

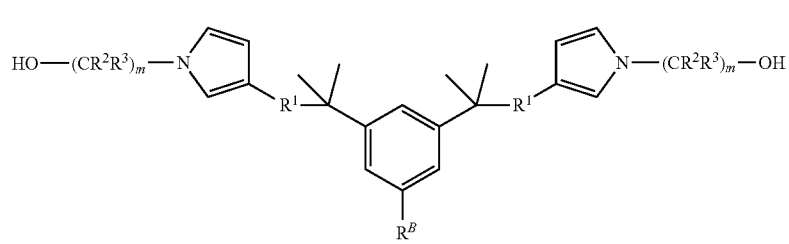

wherein R$^B$ is alkyl.

10. The compound of claim 1, wherein p is 1 or 2.

11. A compound of formula III:

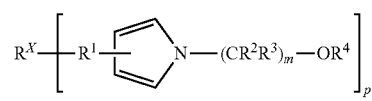

wherein: R$^1$ is a divalent polyolefin group; R$^2$ and R$^3$ are, independently in each —(CR$^2$R$^3$)— unit, hydrogen or alkyl from 1 to 6 carbons; m is an integer from 2 to 20; and R$^4$ is alkyl, alkenyl, alkynyl, aryl, alkaryl, aralkyl, —C(O)R$^5$; —SO$_3$R$^6$, —SO$_2$R$^7$, or —Si(R$^8$)(R$^9$)(R$^{10}$); wherein R$^5$, R$^6$, R$^7$, R$^8$, R$^9$, and R$^{10}$ are each independently, alkyl or aryl, and R$^x$ is

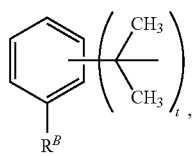

wherein R$^B$ is alkyl; t is an integer from 1-3; and t and p are the same integer.

12. The compound of claim 11, wherein $R^1$ is in the 3-position of the pyrrole ring.

13. The compound of claim 11, wherein $R^1$ is in the 2-position of the pyrrole ring.

14. The compound of claim 11, wherein $R^1$ is a divalent polyisobutylene group.

15. The compound of claim 11, wherein $R^2$ and $R^3$ are hydrogen.

16. The compound of claim 11, wherein m is 2 or 3.

17. The compound of claim 11, wherein p is 1 and $R^X$ is

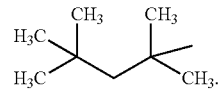

18. The compound of claim 11, wherein $R^4$ is

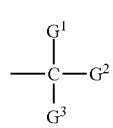

wherein $G^1$ is H or alkyl of 1-3 carbons; and $G^2$ and $G^3$ are each, independently, alkyl of 1-3 carbons.

19. The compound of claim 11, wherein $R^4$ is tert-butyl.

20. The compound of claim 11, wherein p is 1 or 2.

* * * * *